(12) United States Patent
Mao (10) Patent No.: US 11,655,458 B2
(45) Date of Patent: May 23, 2023

(54) TARGET CAPTURING APPARATUS AND MANUFACTURING METHOD THEREOF, AND TARGET DETECTING METHOD

(71) Applicant: BOE TECHNOLOGY GROUP CO., LTD., Beijing (CN)

(72) Inventor: Defeng Mao, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 937 days.

(21) Appl. No.: 16/468,100

(22) PCT Filed: Oct. 17, 2018

(86) PCT No.: PCT/CN2018/110672
§ 371 (c)(1),
(2) Date: Jun. 10, 2019

(87) PCT Pub. No.: WO2019/114410
PCT Pub. Date: Jun. 20, 2019

(65) Prior Publication Data
US 2021/0363493 A1     Nov. 25, 2021

(30) Foreign Application Priority Data
Dec. 15, 2017  (CN) .......................... 201711350244.2

(51) Int. Cl.
*G01N 33/569*  (2006.01)
*B01L 3/00*  (2006.01)
*C12N 5/09*  (2010.01)

(52) U.S. Cl.
CPC ............ *C12N 5/0693* (2013.01); *B01L 3/502* (2013.01); *G01N 33/56966* (2013.01); *B01L 2200/026* (2013.01)

(58) Field of Classification Search
None
See application file for complete search history.

(56) References Cited

U.S. PATENT DOCUMENTS

2008/0026373 A1* 1/2008 Rodionova ...... G01N 33/54373
435/6.1
2010/0255479 A1  10/2010 Mikolajczyk et al.
(Continued)

FOREIGN PATENT DOCUMENTS

CN    101868730 A   10/2010
CN    102227637 A   10/2011
(Continued)

OTHER PUBLICATIONS

CN106867867A English translation; Urine exfoliated tumor cell micro-fluidic chip detection technology aiming at urothelium carcinoma (Year: 2017).*
(Continued)

*Primary Examiner* — Rebecca M Giere
*Assistant Examiner* — Xiaoyan Zou
(74) *Attorney, Agent, or Firm* — Dilworth & Barrese, LLP.; Michael J. Musella, Esq.

(57) ABSTRACT

Embodiments of the present disclosure provide a target capturing apparatus and a manufacturing method thereof, and a target detecting method. The target capturing apparatus includes a cavity structure, the cavity structure includes: an inlet portion, an outlet portion and a capture region positioned between the inlet portion and the outlet portion, and the capture region includes a capture component, and a combination specifically combined with a to-be-captured target is included in the capture component so as to capture the target in a sample entering the cavity structure.

16 Claims, 3 Drawing Sheets

(56) References Cited

U.S. PATENT DOCUMENTS

| | | |
|---|---|---|
| 2011/0294187 A1 | 12/2011 | Toner |
| 2012/0003725 A1 | 1/2012 | Lim |
| 2012/0129192 A1 | 5/2012 | Yazdanpanah et al. |
| 2013/0074613 A1* | 3/2013 | Jeon .................. G01N 1/34 |
| | | 73/864 |
| 2015/0196913 A1 | 7/2015 | Liu et al. |
| 2015/0377753 A1* | 12/2015 | Toner .............. G01N 33/54366 |
| | | 436/178 |
| 2017/0315121 A1* | 11/2017 | Wegener .............. A61M 1/362 |

FOREIGN PATENT DOCUMENTS

| | | |
|---|---|---|
| CN | 102414562 A | 4/2012 |
| CN | 102732415 A | 10/2012 |
| CN | 102925337 A | 2/2013 |
| CN | 104371919 A | 2/2015 |
| CN | 105462834 A | 4/2016 |
| CN | 105861297 A | 8/2016 |
| CN | 106281962 A | 1/2017 |
| CN | 106867867 A | 6/2017 |
| CN | 107338185 A | 11/2017 |
| CN | 107402295 A | 11/2017 |
| CN | 108103022 A | 6/2018 |
| WO | 2010111388 A3 | 9/2010 |

OTHER PUBLICATIONS

International Search Report and Written Opinion dated Dec. 29, 2018 from State Intellectual Property Office of the P.R. China.
First Chinese Office Action in Chinese Application No. 201711350244.2 dated Apr. 3, 2020.

\* cited by examiner

TARGET CAPTURING APPARATUS AND MANUFACTURING METHOD THEREOF, AND TARGET DETECTING METHOD

TECHNICAL FIELD

Embodiments of the present disclosure relate to a target capturing apparatus and a manufacturing method thereof, and a target detecting method.

BACKGROUND

Tumor cells intruding into blood circulation are called as Circulating Tumor Cells (CTCs). In recent years, with the development of micro-nano processing technology and microfluidic technology, separating and counting technologies of the CTCs have been applied in the early stages of diseases, and the CTCs are helpful for identification of benign or malignant tumors and estimation and judgment of metastatic risk. Therefore, CTC sorting based on the microfluidic technology has become a research focus and many methods for separating and detecting CTCs have been developed.

SUMMARY

Embodiments of the present disclosure provide a target capturing apparatus and a manufacturing method thereof, and a target detecting method.

At a first aspect, an embodiment of the present disclosure provides a target capturing apparatus, the target capturing apparatus comprises a cavity structure including: an inlet portion and an outlet portion; and a capture region positioned between the inlet portion and the outlet portion, and the capture region includes a capture component, and a combination specifically combined with a to-be-captured target is included in the capture component so as to capture the target in a sample entering the cavity structure.

For example, the cavity structure further includes a mixing region, the mixing region is positioned between the inlet portion and the capture region, the mixing region includes a mixing component, and the mixing component is configured to uniformly mixing the sample which enters from the inlet portion and includes the to-be-captured target with the target.

For example, the capture region is configured to have an inclined bottom surface, and one end of the inclined bottom surface, which is positioned at the inlet portion, is higher than one end of the inclined bottom surface, which is positioned at the outlet portion.

For example, the capture component includes a plurality of capture units, and the combination is arranged in each of the plurality of capture units; and the capture unit has a first opening and a second opening, the first opening is larger than the second opening, and the first opening faces a side where the inlet portion is positioned.

For example, the capture unit includes a first arc body and a second arc body which are arranged oppositely, sides of the first arc body and the second arc body, which face the inlet portion, are spaced by a first distance so as to form the first opening, and sides of the first arc body and the second arc body, which face the outlet portion, are spaced by a second distance so as to form the second opening.

For example, end portions of the first arc body and the second arc body are round and smooth end portions.

For example, the first opening faces the mixing region at a preset included angle.

For example, a size of the combination is smaller than a size of the first opening, and a size of the target is greater than a size of the second opening and smaller than the size of the first opening.

For example, a size of the capture unit is set to enable only one target to be accommodated therein.

For example, the first arc body and the second arc body respectively are a first spherical shell and a second spherical shell of which thicknesses are uniform or the thicknesses are inconsistent.

For example, under a condition that the first spherical shell and the second spherical shell are combined, the first spherical shell and the second spherical shell form a complete spherical shell.

For example, the preset included angle is 0 degree to 90 degrees.

For example, the first opening and the second opening are circle openings, sizes of the first and second openings are diameters of the circles, and sizes of the target and the combination are the diameters.

For example, the target includes Circulating Tumor Cells (CTCs), the sample includes a disembodied biological sample, and the combination includes an antibody combined with the CTCs.

For example, the disembodied biological sample includes disembodied tissues or cells, Formalin fixed tissues or cells, paraffin-embedded tissues or cells, blood, or body fluid.

For example, the mixing component includes at least one row of column structures, each row in the at least one row of column structures is perpendicular to a direction from the inlet portion to the outlet portion, and the column structures in an identical row are uniformly arranged at a first interval.

For example, the column structure includes at least one type of a cylinder structure, a cone structure or a rhombohedron structure, and the column structures in the identical row are the same or different in shape.

For example, the column structures in different rows are staggered.

For example, a width of the first interval is greater than the size of one target and smaller than a total size of two targets so as to enable only one target to pass through.

For example, the target capturing apparatus further comprises an advection region being positioned between the mixing region and the capture region and having a horizontal bottom surface, and the advection region is configured to control a flow rate of the sample to enter the capture region.

For example, the column structure extends upwards perpendicular to a bottom of the cavity structure.

For example, the mixing region, the advection region and the capture region have the same horizontal heights.

At a second aspect, an embodiment of the present disclosure provides a target detecting method adopting the target capturing apparatus according to the first aspect, the method comprises: providing the sample mixed with a target to the target capturing apparatus from the inlet portion; enabling the sample to flow through the capture region and flow out of the outlet portion, collecting the sample flowing out of the outlet portion; and carrying out microscopic observation analysis on the target in the capture region, which is captured by the capture component, and carrying out counting.

At a third aspect, an embodiment of the present disclosure provides a manufacturing method of the target capturing apparatus according to the first aspect, the method comprises manufacturing the cavity structure including the inlet portion, the outlet portion and the capture region; forming the capture component in the capture region; and fixing the combination to the capture component.

For example, the forming the capture component in the capture region includes forming the capture component in the capture region by utilizing plasma chemical vapor deposition; and the fixing the combination to the capture component includes fixing the combination to the capture component by utilizing an adhesive.

BRIEF DESCRIPTION OF THE DRAWINGS

In order to clearly illustrate the technical solution of the embodiments of the invention, the drawings of the embodiments will be briefly described in the following; it is obvious that the described drawings are only related to some embodiments of the invention and thus are not limitative of the invention.

DETAILED DESCRIPTION

Embodiments of the present disclosure will be in detail described hereinafter, and examples of the embodiments are shown in the drawings, in which the same or similar reference number is denoted as the same or similar members or the members with the same or similar function throughout. The described embodiments in conjunction with the accompanying drawings of the present disclosure are exemplary, only is used to explain the present disclosure and do not intend to limit the present disclosure.

In the description, the description with referring to the terms "an embodiment", "some embodiments", "example", "specific example" or "some examples" means that the specific feature, structure, material or character described with connection with the embodiment or example is included in at least one embodiment or example of the present disclosure. In the description, the schematic description of the above terms is not necessary to direct to the same embodiment or example. The described feature, structure, material or character may be combined in any suitable manner in any or a plurality of embodiments or examples. Further, in case of no conflict, different embodiments or examples and features in different embodiments or example described in the specification can be combined.

Further, the terms, such as "first," "second," or the like, which are used in the description and the claims of the present disclosure, are used only for describing and are not intended to indicate or imply the relative importance or implicitly indicate the amount of the features. Thus, the features defined by "first," "second," may explicitly indicate or implicitly includes at least one feature. In the description of the present disclosure, Unless otherwise defined, "a plurality of" means two or more.

A method for magnetically sorting CTCs is complicated in operation, takes a long time and requires a large blood sample volume (more than 5 mL), mononuclear cells need to be preprocessed and enriched, and both the amount and the purity of the obtained CTCs are relatively low, and thus, sensitivity of detecting the CTCS and discrimination on diseases can be directly influenced.

Hereinafter, the specific embodiments of the present disclosure will be described in detail in connection with the drawings, but are not limitative of the present disclosure.

It should be understood that various modifications can be made to the embodiments disclosed herein. Therefore, the above-mentioned specification should not be considered as the limitation, but merely used as an example of the embodiments. Those skilled in the art will think of other modifications in the scope and spirit of the present disclosure.

The drawings included in the specification and constituting one part of the specification show the embodiments of the present disclosure, and are used for explaining the principle of the present disclosure together with the above general description of the present disclosure and the detailed description of the embodiments given below.

By description on preferred forms of the embodiments given as non-limited examples with reference to the drawings, these and other features of the present disclosure will become obvious.

It should be understood that the present disclosure has been described with reference to some specific examples, but those skilled in the art can definitely implement many other equivalent forms of the present disclosure, which have the features according to the claims and thus are all within the scope defined hereby.

When in connection with the drawings, in consideration of the detailed description below, the above-mentioned and other aspects, features and advantages of the present disclosure will become more obvious.

The specific embodiments of the present disclosure will be described hereafter with reference to the drawings; however, it should be understood that the disclosed embodiments merely are examples of the present disclosure, and can be implemented in various modes. Well-known and/or repeated functions and structures are not described in detail so as to avoid a case that unnecessary or redundant details make the present disclosure fuzzy. Therefore, the specific structural and functional details disclosed herein are not intended to limit, but are merely used as a basis and representative basis of the claims for teaching those skilled in the art to diversely use the present disclosure by substantially random proper detail structures.

This specification may use phrases such as "in one embodiment", "in another embodiment", "in yet another embodiment" or "in other embodiments", which all can refer to one or more of the same or different embodiments of the present disclosure.

Hereinafter, the embodiments of the present disclosure will be illustrated in detail with reference to the drawings. An embodiment of the present disclosure provides a target capturing apparatus. According to the target capturing apparatus, a specific combination capable of capturing a target may be arranged in a capture region within a cavity structure, and the specific combination can be combined with the target in a sample injected into the cavity structure, so that effective separation between the target in the sample and other substances is implemented, and a capture rate of the target can be greatly improved.

Figure 1:
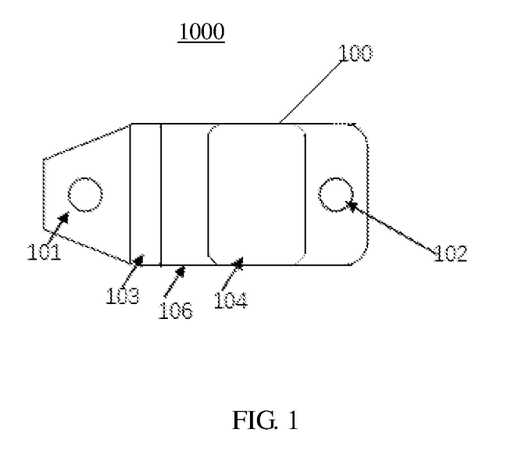
FIG. 1 is a structural schematic diagram of a target capturing apparatus in an embodiment of the present disclosure.

FIG. 1 shows a structural schematic diagram of a target capturing apparatus in an embodiment of the present disclosure, wherein the target capturing apparatus 1000 may include a cavity structure 100, and an inlet portion 101 and an outlet portion 102 may be disposed on the cavity structure 100. The inlet portion 101 is used for injecting a sample including a target. For example, the target in the embodiment of the present disclosure may include CTCs, correspondingly, the sample includes a disembodied biological sample, and the disembodied biological sample may include disembodied tissues or cells, or Formalin fixed tissues or cells, or paraffin-embedded tissues or cells, or blood, or body fluid.

In addition, the outlet portion 102 is used for discharging substances other than the target in the sample, such as blood components of white blood cells, red blood cells and the like in the sample, of which the CTCs are screened out. The inlet portion 101 and the outlet portion 102 are respectively disposed on both opposite sides of the cavity structure.

The cavity structure 100 in the embodiment of the present disclosure may comprise a capture region 104 between the inlet portion 101 and the outlet portion 102. The capture region 104 may be used for screening the target from the sample, such as screening CTCs from plasma stock solution, and discharging other tissues such as red blood cells, white blood cells, exosome and the like in plasma through the outlet portion 102, wherein a capture component may be included in the capture region 104, and a combination specifically combined with a to-be-captured target may be included in the capture component so as to capture the target in the sample entering the cavity structure. In other words, after the sample enters the cavity structure from the inlet portion 101 and enters the capture region 104, the specific combination in the capture component in the capture region 104 can be combined with the target to capture the target. For example, the combination in the embodiments of the present disclosure may include an antibody capable of being combined with the CTCs, and by arrangement of the antibody, the CTCs in blood injected into the cavity structure can be captured.

Figure 2:
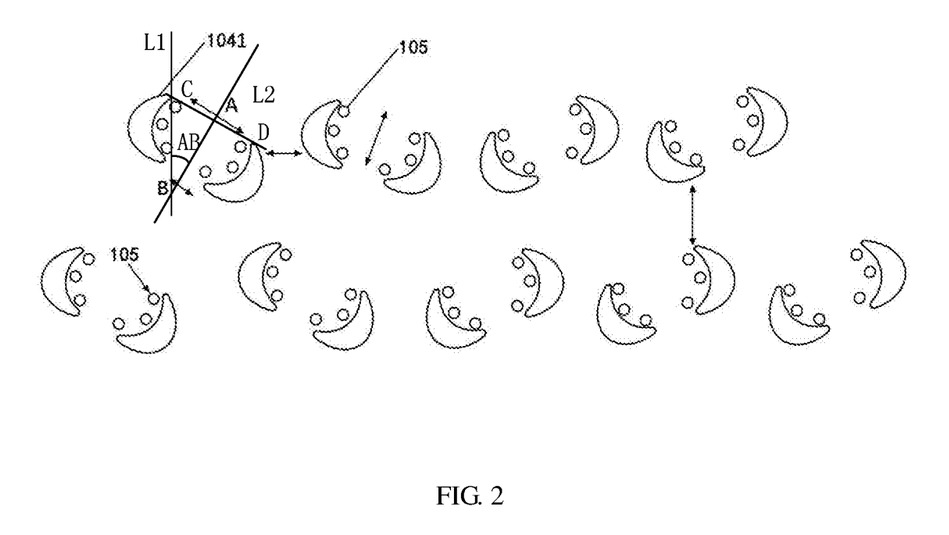
FIG. 2 is a structural schematic diagram of a capture component in an embodiment of the present disclosure.
Figure 3:
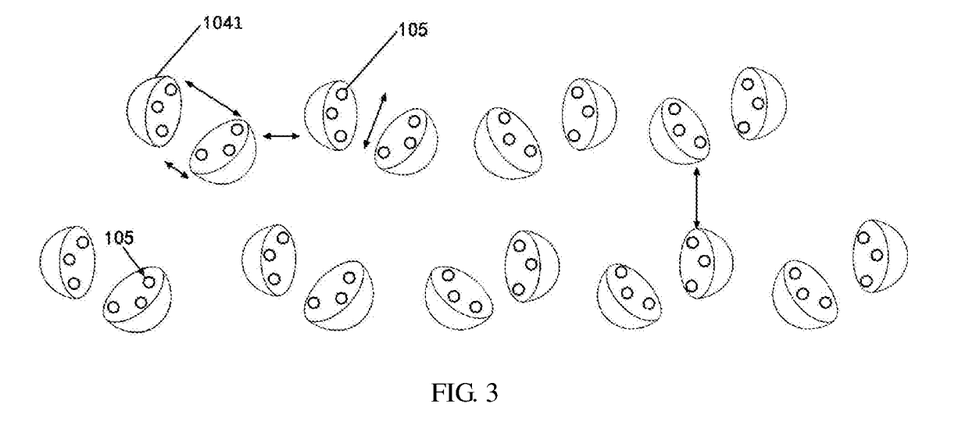
FIG. 3 is a stereoscopic structural schematic diagram of a capture component in an embodiment of the present disclosure.

FIG. 2 shows a structural schematic diagram of a capture region in an embodiment of the present disclosure, and FIG. 3 shows a stereoscopic structural schematic diagram of a capture unit in an embodiment of the present disclosure. A capture component for screening and capturing a target may be arranged in the capture region 104 in the embodiments of the present disclosure, and a specific combination 105 for being combined with the target is arranged in the capture component. By the combination 105, the target entering the capture region can be effectively left in the capture region so as to implement capturing and screening on the target. For example, the above-mentioned specific combination 105 may be a CTC specific antibody for absorbing CTCs in antibody plasma stock solution.

Exemplarily, the capture component may be directly formed on the bottom surface of the cavity structure according to methods of Plasma Enhanced Chemical Vapor Deposition (PECVD) and the like.

Exemplarily, the capture component in the embodiments of the present disclosure includes a plurality of capture units 1041, the capture unit 1041 may form a space for leading in or leading out sample components, the combination 105 may be arranged in a space formed by each capture unit 1041, each capture unit 1041 has a first opening A and a first opening B, the first opening A is larger than the second opening B, the first opening A faces one side where the inlet portion 101 is positioned, and positions of the first opening A and the second opening B may be opposite.

The first opening A faces the inlet portion 101, and thus, the sample flowing to the capture region 104 from the inlet portion 101 can enter the capture unit 1041, and the combination 105 is arranged in the capture unit 1041 (for example, a plurality of combinations 105 may be arranged), and thus, to-be-captured targets entering the capture unit 1041 can be sufficiently absorbed by utilizing those combinations 105 and the targets are retained in the capture unit 1041, and other substance components can flow out of the capture unit 1041 through the second opening B or the first opening A.

Exemplarily, a size of the combination 105 in the embodiments of the present disclosure is smaller than an opening size of the first opening A, and the combination 105 is fixed to the capture unit 1041 by adhesion for example so as not to flow out of the capture unit 1041.

Exemplarily, the capture unit in the embodiments of the present disclosure may be a shell body with a first opening and a second opening, the first opening and the second opening may be round openings, sizes of the first opening and the second opening are diameters, and the capture unit may be formed by firstly cutting the shell body with the openings, placing the combination 105 in the shell body and then connecting them.

In addition, the first opening A of the capture unit 1041 in the embodiments of the present disclosure may face a direction where an opening portion 101 is positioned according to a preset included angle. The preset included angle ranges from 0 degree to 90 degrees. Exemplarily, as shown in FIG. 2, an included angle of the first opening A is AB, one side of the included angle is a vertical line led out of an uppermost endpoint of an uppermost arc body in left and right arc bodies, which faces the opposite arc body, the other side of the included angle is a midperpendicular of a connection line of the highest points of the left and right arc bodies, and as shown in FIG. 2, one side of the included angle AB is L1 and is a vertical line led out of a highest point of the left arc body, and the other edge of the included angle AB is L2 and is a midperpendicular of a connection line of the highest points C and D of two arc bodies.

Exemplarily, as shown in FIG. 2, the first opening of the capture unit 1041 leftwards or rightwards faces one side where the opening portion 101 is positioned at a preset angle. By setting of the preset angle, sample stock solution flowing to the capture unit 1041 may form a vortex in the capture unit 1041 along a shape of the capture unit, one part of sample stock solution may flow out of the capture unit 1041 through the first opening A, and the other part of sample stock solution flows out of the second opening B, wherein a caliber of the first opening A in the embodiments of the present disclosure can allow one target to enter the capture unit 1041, a caliber of the second opening B is configured to prevent the target to flow out of the second opening B, in addition, a height of the capture unit 1041 allows the target to be accommodated in the space formed by the capture unit, and only one target can be accommodated in the capture unit. In the embodiments of the present disclosure, when the target is a CTC, the CTC is a near round cell with a diameter of 15 µm to 25 µm, and thus, the first opening may have a caliber of 30 µm so as to ensure that the CTC can enter each capture unit, and a height of the capture unit may be 25 µm so as to ensure that each capture unit only can capture the CTC, which facilitates accurate screening; a caliber of the second opening B may be 8 µm, so that a red blood cell with an average diameter of about 7 µm can be guaranteed to flow out of the second opening B or the first opening A of the capture unit; and although a size of a white blood cell is approximate to that of the CTC, the combination 105 such as the antibody is arranged in the capture unit, and thus, although the white blood cell can also enter the capture unit, but the white blood cell cannot be adhered and can be impacted out of the capture unit through the first opening A by a sample subsequently flowing in. In other embodiments of the present disclosure, the caliber of the first opening, the caliber of the second opening and the height of the capture unit may also be configured to other lengths when the target is any other substance, which can be set by those skilled in the art.

As shown in FIG. 2 and FIG. 3, each capture unit 1041 in the embodiments of the present disclosure may be configured to be of an arc structure. The arc structure may include a first arc body and a second arc body which are arranged oppositely, a second interval (the second interval is configured as the first opening A) is formed between one sides of the first arc body and the second arc body which are arranged oppositely, a third interval (the third interval is configured as the second opening B) is formed between the other sides of the first arc body and the second arc body, the second interval is larger than the third interval, and one side where the second interval is located faces one side where the opening portion 101 is positioned, wherein the second interval is configured to allow the target to pass through, and the third interval is configured to allow a substance of which a size is smaller than that of the target to pass through, but not allow the target to pass through. The combination is arranged between the first arc body and the second arc body of each set of arc structure. The first arc body in the embodiments of the present disclosure may be configured as a hemispherical arc body, and may also be configured to have other shapes.

Exemplarily, the first arc body and the second arc body respectively are a first spherical shell and a second spherical shell of which thicknesses are uniform or the thicknesses are inconsistent.

Exemplarily, the first spherical shell and the second spherical shell may be combined to form a complete spherical shell.

Exemplarily, the first arc body and the second arc body may be of a roughly arc structure with an irregular surface.

Exemplarily, a bottom surface of the capture region 104 may be parallel to that of the cavity structure.

In addition, in another embodiment of the present disclosure, the capture region may be configured to have an inclined bottom surface, and one side of the inclined bottom surface, which is close to the inlet portion 101, is higher than one side of the inclined bottom surface, which is close to the outlet portion 102. Therefore, a contact surface area between the combination 105 and the sample stock solution can be increased, a sample flux can be improved, and it is helpful for achieving a smaller combination number, a shorter detection period and higher capture efficiency.

Figure 4:
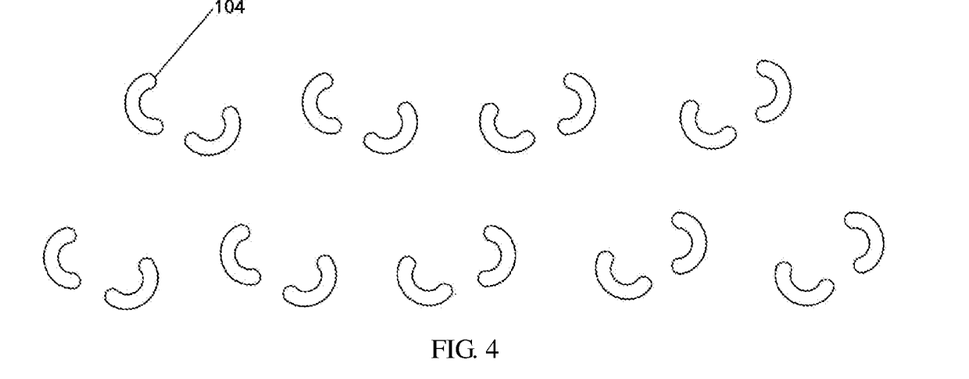
FIG. 4 is a structural schematic diagram of a capture component in another embodiment of the present disclosure.

It should be noted herein that: the first arc body and the second arc body of the capture unit in the embodiments of the present disclosure may be configured to have round and smooth end portions, such as round and smooth top ends, and as shown in FIG. 4, the capture unit in the capture component in the embodiment of the present disclosure may also be configured to be of a structure with a round and smooth opening, i.e., both the first arc body and the second arc body of the capture unit have flat and smooth top ends, and by the configuration, damage of sharp surfaces of the first arc body and the second arc body to the target component in the sample can be prevented. In addition, one side of the capture unit, which faces the inlet portion 101, has a corner structure, so that the sample stock solution forms the vortex when entering the capture region 104, the sample stock solution is more uniform, and meanwhile, the sample can also be more sufficiently in contact and in combination with the combination 105 in the capture unit 1041.

As shown in FIG. 1, a mixing region 103 is also arranged between the opening portion 101 and the capture region 104 of the cavity structure, wherein the mixing region 103 may be provided with a mixing component, the mixing component can uniformly mix a sample stock solution injected from the inlet portion 101, the sample stock solution may include an disembodied biological sample, and the disembodied biological sample includes disembodied tissues or cells, or Formalin fixed tissues or cells, or paraffin-embedded tissues or cells, or blood, or body fluid. For example, the CTC and other blood components may be included in the sample.

Figure 5:
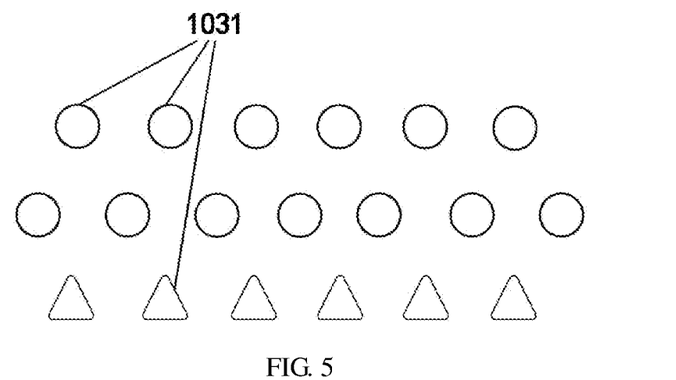
FIG. 5 is a structural schematic diagram of a mixing component in an embodiment of the present disclosure.
Figure 6:
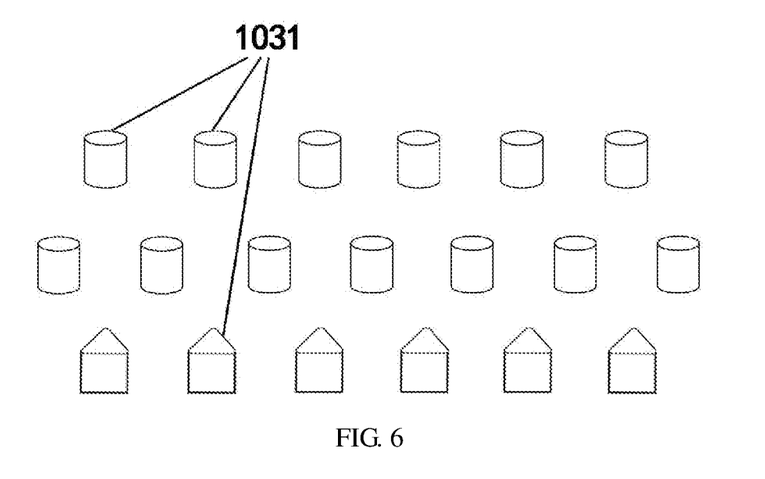
FIG. 6 is a stereoscopic structural schematic diagram of a mixing component in an embodiment of the present disclosure.

FIG. 5 shows a structural schematic diagram of a mixing region in an embodiment of the present disclosure, and FIG. 6 shows a stereoscopic structural schematic diagram of a mixing region in an embodiment of the present disclosure, wherein a mixing component of the mixing region 103 may include at least one row of column structures 1031 extending upwards from the bottom of the cavity structure 100, a plurality of rows of column structures 1031 may be arranged along a direction from the inlet portion to the outlet portion, the arrangement direction of each row of column structures 1031 may be perpendicular to a flowing direction of plasma stock solution, i.e., perpendicular to a direction from the inlet portion to the outlet portion, and an interval between two adjacent column structures 1031 in each row may be all a first interval. A width of the first interval is greater than a size of one target and smaller than a total size of two targets, and is configured to only allow one target to pass through the first interval, and for example, the first interval may be 30 or 40 micrometers (a diameter of the CTC is 15 micrometers to 25 micrometers). In the embodiments of the present disclosure, the first interval only allows one target to pass through, and thus, when the sample stock solution enters the mixing region 103, under the action of the first interval between the column structures 1031, targets uniformly arranged in a column form can be formed, so that the sample stock solution containing the targets can be uniformly mixed.

Further, in the embodiments of the present disclosure, a plurality of rows of column structures 1031 may be arranged in the mixing region 103, so as to further improve mixing uniformity of the plasma stock solution. Each row of column structures may be staggered according to the arrangement of rows, and for example, the column structures 1031 on a second row may be arranged at positions (as shown in FIG. 5) corresponding to intervals between the column structures 1031 on a first row, so that mixing uniformity can be further improved.

Figure 7:
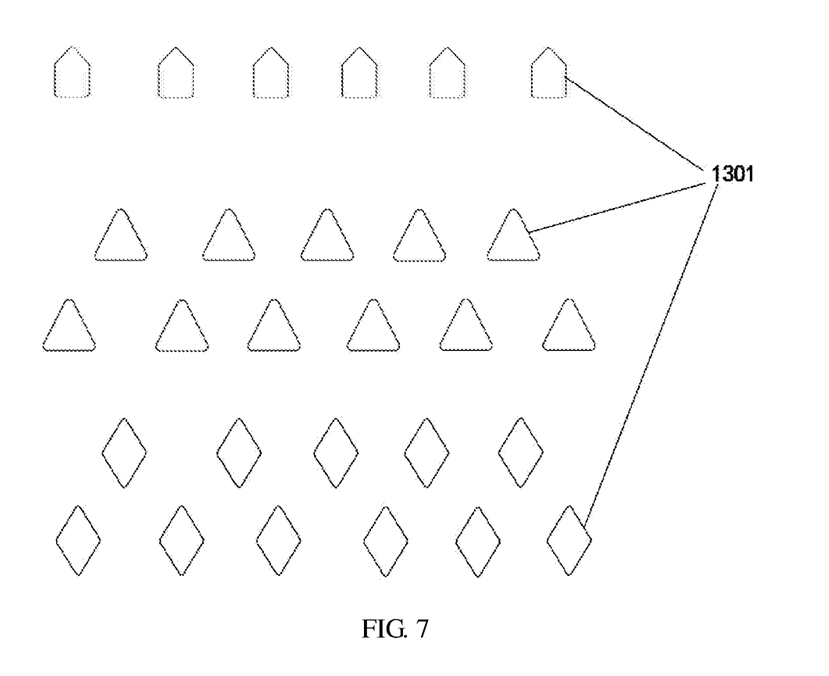
FIG. 7 is a structural schematic diagram of a mixing component in another embodiment of the present disclosure.

In addition, in the embodiments of the present disclosure, the shapes of each row of column structures 1031 in the mixing region may include at least one type of a cylinder structure, a cone structure and a rhombohedron structure (as shown in FIG. 7), and each column structure on the same row may be the same or different in shape. The column structures in the different row may be the same or different in shape. By the above-mentioned configuration, the sample stock solution passing through the mixing region can be uniformly mixed and flow to the capture region 104.

In addition, as shown in FIG. 1, in the embodiment of the present disclosure, an advection region 106 may also be included between the mixing region 103 and the capture region 104, and the advection region 106 is configured as a cavity. The advection region 106 in the embodiments of the present disclosure can enable a flow rate of the plasma stock solution flowing out of the mixing region 103 to be more uniform and lower, so that the stock solution flowing to the capture region 104 is more uniform. The advection region 106 may be configured to have a horizontal bottom surface from the mixing region to the capture region, and a length of the advection region is 100 micrometers. By the configuration, a longitudinal length of the advection region not only can ensure that a to-be-detected sample is uniform in flowing rate, but also can ensure that the to-be-detected sample enters the capture region at a certain initial speed.

Exemplarily, FIG. 1 shows a schematic planar graph of the target capturing apparatus, in order to facilitate illustration, vertical lines are shown among the mixing region 103, the capture region 104 and the advection region 106, but those vertical lines only means to represent different regions, but do not indicate that there are boundary or isolation board structures among the regions, and actually, there are no isolation boards among the mixing region 103, the capture region 104 and the advection region 106, but the mixing region 103, the capture region 104 and the advection region 106 are directly in smooth transition, so that damage to the to-be-detected sample, which is caused by corners, can be avoided; and the mixing region 103, the capture region 104 and the advection region 106 can have the same horizontal heights with respect to the bottom surface of the cavity structure, or ends of the mixing region 103, the advection region 106 and the capture region 104, which are close to the inlet portion 101, have the same horizontal heights, one end of the capture region 104, which is close to the outlet portion 102, is lower than one end of the capture region 104, which is close to the inlet portion 101, and one end of the capture region 104, which is close to the outlet portion 102, and the outlet portion 102 are positioned at the same horizontal height, so as to facilitate sample flowing.

An embodiment of the present disclosure further provides a target detecting method, adopting the target capturing apparatus as the above and including: providing the sample mixed with a target to the target capturing apparatus from the inlet portion; and enabling the sample to flow through the capture region and flow out of the outlet portion, collecting the sample flowing out of the outlet portion, carrying out microscopic observation analysis on the target in the capture region, which is captured by the capture component, and carrying out counting.

Exemplarily, the target in the capture region may be analyzed by a microscope and the target is counted.

An embodiment of the present disclosure further provides a manufacturing method of the target capturing apparatus as the above, including:

Manufacturing the cavity structure including the inlet portion, the outlet portion and the capture region;

Forming the capture component in the capture region; and

Fixing the combination to the capture component.

Exemplarily, forming the capture component in the capture region includes:

Forming the capture component in the capture region by utilizing plasma chemical vapor deposition; and Fixing the combination to the capture component includes:

Fixing the combination to the capture component by utilizing an adhesive.

Exemplarily, the combination may also be fixed to the capture component by other methods, such as methods of hot pressing and the like.

Exemplarily, the capture component may also be formed by a polymethyl methacrylate (PMMA) material through a photolithography process, which is not limited by the embodiments of the present disclosure.

From the above, it can be known on the basis of the disclosed embodiments that the embodiments of the present disclosure have the advantageous effects that: according to the embodiments of the present disclosure, screening and capturing of the target are carried out by the capture region, and the specific combination for absorbing the target is included in the capture component arranged in the capture region, so that the target can be conveniently captured and the capture rate of the target can also be effectively improved.

It can be clearly noted for those skilled in the art that for the convenience of the description and briefness, an electronic device being applied with the above data processing method may refer to the corresponding description in product embodiments as mentioned above, which is not repeated here.

What are described above is related to the specific embodiments of the disclosure only and not limitative to the scope of the disclosure. The protection scope of the disclosure shall be based on the protection scope of the claims. Any modification and equivalent replacement may be made by those skilled in the art within the substantial protection scope of the embodiments of the present disclosure, which is regarded as falling within the protection scope of embodiments of the present disclosure.

The application claims priority to the Chinese patent application No. 201711350244.2, filed Dec. 15, 2017, the disclosure of which is incorporated herein by reference as part of the application.

The invention claimed is:

1. A target capturing apparatus, comprising:
a cavity structure, including:
an inlet portion and an outlet portion; and
a capture region, positioned between the inlet portion and the outlet portion,
wherein the capture region includes a capture component, and a combination which will specifically bind to a to-be-captured target is included in the capture component so as to capture the target in a sample entering the cavity structure,
wherein the capture region is configured to have an inclined bottom surface, and one end of the inclined bottom surface, which is positioned at the inlet portion, is higher than one end of the inclined bottom surface, which is positioned at the outlet portion,
wherein the capture component includes a plurality of capture units, and the combination is arranged in each of the plurality of capture units; and the capture unit has a first opening and a second opening,
wherein each of the plurality of capture units includes only a first arc body and a second arc body which are arranged oppositely, sides of the first arc body and the second arc body, which face the inlet portion, are spaced by a first distance so as to form the first opening, and sides of the first arc body and the second arc body, which face the outlet portion, are spaced by a second distance so as to form the second opening,
wherein the first arc body and the second arc body respectively are a first spherical shell and a second spherical shell of which thicknesses are uniform or the thicknesses are inconsistent, wherein under a condition that the first spherical shell and the second spherical shell are combined, the first spherical shell and the second spherical shell form a complete spherical shell.

2. The target capturing apparatus according to claim 1, wherein the cavity structure further includes:
   a mixing region, the mixing region being positioned between the inlet portion and the capture region,
   the mixing region including a mixing component, and the mixing component being configured to uniformly mixing the sample which enters from the inlet portion and includes the to-be-captured target with the target.

3. The target capturing apparatus according to claim 1, wherein the first opening is larger than the second opening, and the first opening faces a side where the inlet portion is positioned.

4. The target capturing apparatus according to claim 1, wherein end portions of the first arc body and the second arc body are round and smooth end portions.

5. The target capturing apparatus according to claim 3, wherein the first opening faces the mixing region at a preset included angle, and the preset included angle is 0 degree to 90 degrees.

6. The target capturing apparatus according to claim 3, wherein a size of the combination is smaller than a size of the first opening, and a size of the target is greater than a size of the second opening and smaller than the size of the first opening.

7. The target capturing apparatus according to claim 6, wherein a size of the capture unit is set to enable only one target to be accommodated therein.

8. The target capturing apparatus according to claim 3, wherein the first opening and the second opening are circle openings, sizes of the first and second openings are diameters of the circles, and sizes of the target and the combination are the diameters.

9. The target capturing apparatus according to claim 1, wherein the target includes Circulating Tumor Cells (CTCs), the sample includes a disembodied biological sample, and the combination includes an antibody combined with the CTCs.

10. The target capturing apparatus according to claim 2, wherein the mixing component includes at least one row of column structures, each row in the at least one row of column structures is perpendicular to a direction from the inlet portion to the outlet portion, and the column structures in an identical row are uniformly arranged at a first interval.

11. The target capturing apparatus according to claim 10, wherein the column structures in different rows are staggered.

12. The target capturing apparatus according to claim 10, wherein a width of the first interval is greater than the size of one target and smaller than a total size of two targets so as to enable only one target to pass through.

13. The target capturing apparatus according to claim 2, further comprising:
   an advection region, being positioned between the mixing region and the capture region and having a horizontal bottom surface,
   wherein the advection region is configured to control a flow rate of the sample to enter the capture region.

14. A target detecting method, adopting the target capturing apparatus according to claim 1, comprising:
   providing the sample mixed with a target to the target capturing apparatus from the inlet portion; and
   enabling the sample to flow through the capture region and flow out of the outlet portion, collecting the sample flowing out of the outlet portion,
   carrying out microscopic observation analysis on the target in the capture region, which is captured by the capture component, and carrying out counting.

15. A manufacturing method of the target capturing apparatus according to claim 1, comprising:
   manufacturing the cavity structure including the inlet portion, the outlet portion and the capture region;
   forming the capture component in the capture region; and
   fixing the combination to the capture component.

16. The manufacturing method according to claim 15, wherein the forming the capture component in the capture region includes:
   forming the capture component in the capture region by utilizing plasma chemical vapor deposition; and
   the fixing the combination to the capture component includes:
   fixing the combination to the capture component by utilizing an adhesive.

* * * * *